(12) United States Patent
Bufler

(10) Patent No.: US 9,066,995 B2
(45) Date of Patent: Jun. 30, 2015

(54) BONE SUBSTITUTE MATERIAL

(75) Inventor: Michael Alexander Bufler, Emmenbruecke (CH)

(73) Assignee: GEISTLICH PHARMA AG, Wolhusen (CH)

( * ) Notice: Subject to any disclaimer, the term of this patent is extended or adjusted under 35 U.S.C. 154(b) by 183 days.

(21) Appl. No.: 13/997,419

(22) PCT Filed: Dec. 21, 2011

(86) PCT No.: PCT/EP2011/006457
§ 371 (c)(1),
(2), (4) Date: Sep. 10, 2013

(87) PCT Pub. No.: WO2012/084214
PCT Pub. Date: Jun. 28, 2012

(65) Prior Publication Data
US 2013/0345825 A1    Dec. 26, 2013

(30) Foreign Application Priority Data

Dec. 22, 2010 (EP) .................................. 10015924

(51) Int. Cl.
*A61F 2/28* (2006.01)
*A61L 27/12* (2006.01)
*A61L 27/42* (2006.01)
*A61L 27/56* (2006.01)

(52) U.S. Cl.
CPC ............... *A61L 27/425* (2013.01); *A61L 27/56* (2013.01); *A61L 27/12* (2013.01); *A61L 2430/02* (2013.01)

(58) Field of Classification Search
CPC .............. A61F 2/28; A61F 2002/2817; A61F 2002/2853; A61L 27/12; A61L 27/24; A61L 27/46
See application file for complete search history.

(56) References Cited

U.S. PATENT DOCUMENTS

| 4,871,578 | A | 10/1989 | Adam et al. | |
|---|---|---|---|---|
| 6,338,752 | B1 | 1/2002 | Lin et al. | |
| 8,734,524 | B2 * | 5/2014 | Bufler | 623/23.61 |
| 2007/0190083 | A1 | 8/2007 | Scifert et al. | |

FOREIGN PATENT DOCUMENTS

| EP | 0285826 A2 | 10/1988 |
|---|---|---|
| WO | 9741273 A1 | 11/1997 |

OTHER PUBLICATIONS

J. E. Zerwekh et al.: "Fibrillar collagen-biphasic calcium phosphate composite as a bone graft substititute for spinal fusion," Journal of Orthopaedic Research, vol. 10, No. 4, Jul. 1992, pp. 562-572, abstract only.

* cited by examiner

*Primary Examiner* — Bruce E Snow
(74) *Attorney, Agent, or Firm* — Rothwell, Figg, Ernst & Manbeck, P.C.

(57) ABSTRACT

The invention relates to: —a porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm, which is impregnated with collagen fibers at a weight ratio of said collagen fibers to said porous biphasic calcium phosphate/hydroxyapatite (CAP/HAP) bone substitute material of at least 2%, —a process of preparing the above porous CAP/HAP bone substitute material, which comprises (a) mixing a slurry of collagen fibers and a porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm, and (b) eliminating the water by vacuum suction, —an implant which comprises a porous collagen matrix surrounding and impregnating particles or granules of porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm, —the use of the above bone substitute material as implant or prosthesis for bone formation, bone regeneration, bone repair and/or bone replacement at a defect site in a human or animal.

16 Claims, No Drawings

BONE SUBSTITUTE MATERIAL

CROSS REFERENCE TO RELATED APPLICATIONS

This application is a 35 U.S.C. §371 National Phase Entry Application from PCT/EP2011/006457, filed Dec. 21, 2011, and designating the United States, which claims priority under 35 U.S.C. §119 to European Patent Application No. 10015924 filed Dec. 22, 2010, which is incorporated herein in its entirety.

The invention relates to a new biphasic bone substitute material with a bilayer structure based on calcium phosphate/hydroxyapatite (CAP/HAP) which is impregnated with collagen fibers, a process for preparing that biphasic bone substitute material and the use thereof as implant or prosthesis to support bone formation, bone regeneration, bone repair, bone remodeling and/or bone replacement at a defect site in a human or animal.

Defects in bone structure arise in a variety of circumstances, such as trauma, disease, and surgery and there is still a need for effective repair of bone defects in various surgical fields.

Numerous natural and synthetic materials and compositions have been used to stimulate healing at the site of a bone defect. A well known natural, osteoconductive bone substitute material that promotes bone growth in periodontal and maxillofacial osseous defects is Geistlich Bio-Oss®, commercially available from Geistlich Pharma AG. That material is manufactured from natural bone by a process described in U.S. Pat. No. 5,167,961, which enables preservation of the trabecular architecture and nanocrystalline structure of the natural bone, resulting in an excellent osteoconductive matrix which is not or very slowly resorbed.

Tricalcium phosphate/hydroxyapatite (TCP/HAP) systems and their use as bone substitute materials are described, for example, in U.S. Pat. No. 6,338,752 disclosing a process for preparing a biphasic cement of $\alpha$-TCP/HAP by heating a powder mixture of ammonium phosphate and HAP at 1200-1500° C.

European Patent EP-285826 describes a process for the production of a layer of HAP on metallic and non-metallic bodies for implants by application of a layer of $\alpha$-TCP and completely converting the $\alpha$-TCP layer into HAP by reaction with water of pH 2 to 7 at 80-100° C. The product obtained is a metallic or non metallic body covered with a layer of HAP.

WO 97/41273 describes a process for coating a substrate such as notably hydroxyapatite (HAP) or other calcium phosphates (CAP) with a coating of carbonated hydroxyapatite, i.e. hydroxyapatite wherein phosphate and/or hydroxyl ions are partially replaced by bicarbonate ions, by a process comprising (a) immersing the substrate in a solution of pH 6.8 to 8.0 containing calcium ions, phosphate ions and bicarbonate ions at a temperature lower than 50° C., (b) heating the portion of the solution in contact with the substrate to a temperature of 50 to 80° C. until having a pH greater than 8, (c) maintaining the substrate in contact with the alkali solution obtained in step (b) to form a carbonated hydroxyapatite coating, and (d) taking the substrate off the solution and subjecting the coating to drying. The bicarbonate ions are disclosed to act as inhibitors of hydroxyapatite crystal growth, resulting in non-stoichiometric crystals containing defects and having rather small dimensions, namely 10-40 nm in length and 3-10 nm in width (see page 7, lines 1-7).

The components of calcium phosphate/hydroxyapatite (CAP/HAP) systems, especially TCP/HAP systems differ in their thermodynamic stability. Due to this difference, when CAP/HAP systems are implanted into a mammal, in particular a human patient, the solubility of TCP and other calcium phosphates is higher in the body fluid than the solubility of HAP. The difference in solubility between calcium phosphates and HAP causes a breakdown of the unordered sinter structure of the CAP/HAP system because the better soluble compound CAP (e.g. TCP) is removed quicker than HAP. The sintered interconnection between CAP and HAP produced at high temperatures will also make a remarkable contribution to higher solubility of the device in the physiological environment. Two different types of reactions dominate accelerated in-vivo degradation of such ceramics: Chemical dissolution and biological resorption by cells. Both processes cause dissolution of the ceramic material which furthermore causes a local oversaturation of calcium ions, whereby there are more calcium ions released than calcium ions adsorbed. The natural equilibrium of calcium ions no longer exists, neither in the extracellular matrix nor in the tissue surrounding of the implant. The local disturbance of the natural calcium equilibrium in terms of oversaturation of calcium ions leads to an increased osteoclast activity and therefore to an accelerated ill-controlled resorption of the ceramic material and a risk of adverse inflammation reactions, especially when using a large amount of synthetic bone substitute material.

When bone substitute material Geistlich Bio-Oss® is implanted into a human patient, the natural calcium equilibrium is practically not affected, the concentration of calcium ions on the surface of the material and within the local environment thereof remaining almost constant. Biological resorption of the material hence does not take place or proceeds at a very slow rate without the risk of adverse inflammation reactions.

The objective of the invention disclosed in international patent application No. PCT/EP2010/003590 was to provide a calcium phosphate/hydroxyapatite (CAP/HAP) bone substitute material which, like bone substitute material Geistlich Bio-Oss®, after being set in vivo enables the concentration of calcium ions on the surface of the material and within the local environment thereof to remain almost constant and thus does not lead to an increased osteoclast activity.

Indeed, the natural calcium equilibrium which is necessary for optimal bone regeneration should not be disturbed or destroyed. Moreover the natural calcium concentration equilibrium should be lastingly supported by the bone substitute material until the regeneration process is completed. When those conditions are met there is no increase of osteoclast activity, hence no risk of adverse inflammation reactions.

The above international patent application reports that the above objective was attained by a new biphasic nanocrystalline CAP/HAP bone substitute material with an exactly defined biomimetic bilayer structure obtained under specific conditions as described therein.

Indeed, as shown by observation under fluorescence light microscopy of that new biphasic nanocrystalline CAP/HAP bone substitute material implanted into a mammal, there is no detectable increase of osteoclast activity in the neighborhood of the implant, which indicates the absence of a rise in the calcium ion concentration on the surface of the material and within the local environment thereof.

The new biphasic nanocrystalline CAP/HAP bone substitute material shows very interesting in vivo properties.

The invention of international patent application No. PCT/EP2010/003590 thus relates to a biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm.

The sintered CAP core may comprise tricalcium phosphate (TCP), notably α-TCP (α-$Ca_3(PO_4)_2$) or (β-TCP (β-$Ca_3(PO_4)_2$), and/or tetracalcium phosphate (TTCP) $Ca_4(PO_4)_2O$.

According to a frequently used embodiment the sintered CAP core essentially consists of TCP, α-TCP being preferred.

The epitactically grown layer of nanocrystalline HAP is structurally and chemically nearly identical to the natural human bone mineral.

The epitactically grown layer of nanocrystalline HAP generally has a thickness of at least from 15 to 50 nm, preferably at least from 20 to 40 nm, more preferably at least from 25 to 35 nm. That minimum thickness corresponds to one layer of HAP nanocrystals in epitaxial orientation.

The epitactically grown layer of nanocrystalline HAP may comprise a single or multiple layers of HAP nanocrystals in epitaxial orientation. The thickness of the epitactically grown layer of nanocrystalline HAP, which is related to the number of such layers of HAP nanocrystals in epitaxial orientation, will be selected according to the intended application of the bone substitute material as implant or prosthesis in differently loaded parts of the body. The bone substitute material of the invention is indeed designed to function in vivo as a living-like system progressively transforming the sintered CAP core into hydroxyapatite similar in size and morphology to human bone mineral, the rate of that transformation being dependent on the rate of calcium release by the sintered CAP core, which is to a large extent controlled by the thickness of the epitactically grown layer of nanocrystalline HAP.

The properties of the CAP/HAP bone substitute material are to a large extent controlled by the thickness of the epitactically grown layer of crystalline HAP. The term "properties" includes the ability of the CAP/HAP bone substitute to release a constant concentration of calcium ions to the local environment in vitro and in vivo.

The thickness of the epitactically grown layer of nanocrystalline HAP is related to the ratio of the sintered CAP core material to HAP, said ratio being generally between 5:95 and 95:5, preferably from 10:90 to 90:10.

The CAP/HAP bone substitute material may be a particulate or a granulate, the particles or granules having a desired size and shape. Generally the particles or granules are approximately spherical and have a diameter of 1 to 5000 µm, preferably 10 to 5000 µm, in particular 250 to 5000 µm.

The CAP/HAP bone substitute material may also be a shaped body, e.g. a screw, a nail, a pin or a structure having the profile of an osseous body part such as notably a hip, a clavicle, a rib, a mandible or a skull part. Such a screw, a nail or a pin may be used in reconstructive orthopedic surgery for fixing a ligament to a bone, for example in the knee or the elbow. Such a structure having the profile of an osseous body part may be used in orthopedic surgery as prosthesis for replacing a missing or defective bone or bone part.

The invention of international application No. PCT/EP2010/003590 further relates to a process of preparing the above defined CAP/HAP bone substitute material comprising the steps of a) preparing a sintered CAP core material,
b) immersing the sintered CAP core material in an aqueous solution at a temperature between 10° C. and 50° C. to start the transformation process of CAP to HAP, whereby a uniform and closed epitactically grown layer of nanocrystalline hydroxyapatite is formed on the sintered CAP core material surface, the epitactically grown nanocrystals having the same size and morphology as human bone mineral,
c) stopping the transformation by separating the solid material from the aqueous solution at a time when a uniform and closed coating of at least one nanocrystalline layer of HAP is present but before the transformation process is finished completely,
d) optionally sterilizing the separated material coming from step c).

The sintered CAP core material may comprise tricalcium phosphate (TCP), notably α-TCP (α-$Ca_3(PO_4)_2$) or β-TCP ((β-$Ca_3(PO_4)_2$), and/or tetracalcium phosphate (TTCP) $Ca_4(PO_4)_2O$.

According to a frequently used embodiment the sintered CAP core material essentially consists of TCP, α-TCP being preferred.

The preparation of the sintered CAP core material may be performed by methods known in the art comprising first mixing powders of calcium hydrogen phosphate ($CaHPO_4$), calcium carbonate and/or calcium hydroxide, then calcining and sintering the mixture within an appropriate temperature range, thereby giving a bulk sintered CAP core material (see e.g. Mathew M. et al., 1977, Acta. Cryst. B33: 1325; Dickens B. et al., 1974, J. Solid State Chemistry 10, 232; and Durucan C. et al., 2002, J. Mat. Sci., 37:963).

A bulk sintered TCP core material may thus be obtained by mixing powders of calcium hydrogen phosphate ($CaHPO_4$), calcium carbonate and/or calcium hydroxide in stoichiometric ratio, calcining and sintering the mixture at a temperature in the range of 1200-1450° C., preferably about 1400° C.

A bulk sintered TTCP core material may also be obtained by the above described process.

The bulk sintered CAP material prepared by such methods may be porous with a porosity of 2 to 80 vol % and a wide distribution of pores. The porosity parameters will be selected according to the intended application of the CAP/HAP bone substitute material.

The sintered CAP core material used in step b) may be
- the bulk sintered CAP core material prepared as described above,
- a particulate or granulate of sintered CAP core material obtained from the bulk sintered CAP core material prepared as described above, by using conventional methods such as crushing, grinding and/or milling, and sieving, or
- a preform of sintered CAP core material having a desired shape and size, e.g. a screw, a nail, a pin or a structure having the profile of an osseous body part.

Such a preform of any desired shape and size may be obtained from the bulk sintered core material prepared as described above, by using well known prototyping techniques such as CNC milling or 3D printing (see for example Bartolo P. et al., 2008, Bio-Materials and Prototyping Applications in Medicine, Springer Science New York, ISBN 978-0-387-47682-7; Landers R. et al., 2002, Biomaterials 23(23), 4437; Yeong W.-Y. et al., 2004, Trends in Biotechnology, 22 (12), 643; and Seitz H. et al., 2005, Biomed. Mater. Res. 74B (2), 782).

The aqueous solution of step b) may be pure water, a simulated body fluid or a buffer. Important is that the pH value of the immersing solution of step b) is nearly neutral and remains stable throughout the transformation process, preferably within a pH range from 5.5 to 9.0.

The buffer may be any buffer in the above pH range but is preferably a phosphate buffer with or without calcium, magnesium and/or sodium.

The term "simulated body fluid" refers to any solution that mimics a body fluid. Preferably, the simulated body fluid has an ion concentration similar to that of blood plasma.

The temperature range in step b) is generally between 10° C. and 50° C., preferably between 25 and 45° C., more preferably between 35° C. and 40° C.

The immersing step b) induces in a first phase a first-order phase transition of the CAP core material and therefore the nucleation of HAP nanocrystal precursors. During the second phase the resulting HAP precursors from the first phase will grow and establish a closed (i.e. completely coating) epitactic nanocrystalline composite layer. The first HAP nanocrystal layer must be uniform and closed and epitaxially connected to the sintered CAP core material throughout its external surface, including, in the case of the sintered CAP core material being porous, in the pores thereof.

During a third phase the first-order phase transition may proceed within the newly formed bilayer composite to further transform the sintered CAP core material (TCP or TTCP) into nanocrystalline HAP. During this third step of phase transition calcium ions will be released for a controllable time by a slow diffusion controlled process until a part of the sintered CAP core material has been transformed into nanocrystalline HAP. The transformation time and therefore the rate of calcium release can be controlled by variation of the thickness of the HAP layer.

The epitactically grown nanocrystalline HAP layer of appropriate thickness will be prepared in-vitro, the transformation of CAP into HAP being stopped before it is completed.

As soon as the CAP/HAP bone substitute material is set in vivo the transformation process of CAP into HAP will be reactivated by contact with the body fluids and the bone substitute material will function as a living-like system forming new hydroxyapatite similar in size and morphology to humane bone mineral. During the in vivo phase transformation process the transported calcium ions will be released into the local environment supporting the local calcium equilibrium which is important and beneficial for bone regeneration processes.

Due to different regeneration times of bone defects in differently loaded regions of the body it is important that the rate of calcium release can be controlled. This can be achieved by variation of the thickness of the epitactically grown layer of hydroxyapatite.

Step c) is therefore a very critical step. The exposure time in the aqueous solution of step b) is based upon the thickness of the HAP layer desired. At least one layer of nanocrystalline HAP in epitaxial orientation is necessary. It is essential that the transformation of CAP into HAP is not finished.

The proper exposure time according to the thickness desired can be calculated by using several thermodynamic differential equations well known to the skilled person in the art of calcium phosphates and cement and concrete chemistry.

See for example: Pommersheim, J. C.; Clifton, J. R. (1979) Cem. Conc. Res.; 9:765; Pommersheim, J. C.; Clifton, J. R. (1982) Cem. Conc. Res.; 12:765; and Schlüssler, K. H. Mcedlov-Petrosjan, O. P.; (1990): Der Baustoff beton, VEB Verlag Bauwesen, Berlin.

Transferring the solution of the above mentioned differential equations to the CAP/HAP system enables the prediction of the phase transition of CAP into HAP and the thickness of the layer such that the epitactic layer of HAP can be prepared in a stable and reproducible manner.

Separating the solid material from the aqueous solution is usually performed by filtration and drying, using techniques well known in the art.

The optional sterilizing step d) may be performed by techniques well known in the art such as gamma-irradiation.

Advantages of the CAP/HAP Bone Substitute Material of the Above Invention

The epitactically grown HAP nanocrystals surrounding the sintered CAP core material are identical in size and morphology to the apatite crystals of natural human bone mineral as shown in Table 1 below. Thus the CAP/HAP bone substitute material of the invention successfully mimics the composite or microstructure of bone and is representing a biomimetic material of human bone mineral.

TABLE 1

Comparison of the HAP crystal size and morphology for the CAP/HAP bone substitute of the invention and human bone mineral

| Crystallographic axes (hexagonal space group P63/m) | CAP/HAP of the invention prepared at physiological temperature. Crystal size* [nm] | natural human bone mineral Crystal size* [nm] |
|---|---|---|
| a (1, 0, 0) | 18 (±4) | 15-21 |
| b (0, 1, 0) | 18 (±4) | 15-21 |
| c (0, 0, 1) | 38 (±8) | 34-45 |

*Crystal size analysis has been performed by using TEM (transmission electron microscopy), SPM (scanning probe microscopy techniques) as well as refinement of X-ray diffraction data by using the Bragg method.

The constant concentration of calcium ions results in an improved adhesion of osteoblasts and osteoclasts to the HAP surface in the correct ratio for the osteogenesis and thus to a steady state in the cycle of bone regeneration. A surface is provided to which osteoblasts and osteoclasts readily attach in the correct ratio for bone regeneration.

Furthermore due to its highly controllable surface properties the above CAP/HAP bone substitute material can function as a matrix for bioactive molecules such as extracellular matrix proteins such as notably growth factors for bone regeneration.

It has now been found that the adhesion of osteoblasts and osteoclasts to the HAP surface in the correct ratio for the osteogenesis can be further improved by impregnating the above defined porous CAP/HAP bone substitute material with collagen fibers such as to further mimic the in vivo natural processes of bone formation, bone regeneration, bone repair, bone remodeling and bone replacement by creating an environment closer to that of bone or damaged bone, namely a hydroxyapatite part and an organic matrix comprising collagen fibers.

The collagen fibers are generally fibers of collagen type I, collagen type III or a mixture thereof, or fibers of collagen type II.

Interesting results have been so far obtained in particular with fibers derived from pig skin which are a mixture of collagen I and collagen III, collagen I being predominant.

The present invention thus concerns a porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm, which is impregnated with collagen fibers at a weight ratio of said collagen fibers to said porous biphasic calcium phosphate/hydroxyapatite (CAP/HAP) bone substitute material of at least 2%.

Generally the impregnation with collagen fibers takes place throughout the external surface of the uniform and closed epitactically grown layer of nanocrystalline HAP, including inside the pores, as shown by scanning electron microscopy.

The weight ratio of said collagen fibers to said porous biphasic calcium phosphate/hydroxyapatite (CAP/HAP) bone substitute material is preferably at least 5%, in particular at least 8%. That weight ratio is generally from 2 to 80%, preferably from 5 to 50%, in particular from 8 to 25%.

According to an interesting embodiment the collagen fibers are fibers of collagen type I, collagen type III or a mixture thereof.

The epitactically grown layer of nanocrystalline HAP generally has a thickness of at least from 15 to 50 nm, preferably at least from 20 to 40 nm, more preferably at least from 25 to 35 nm. That minimum thickness corresponds to one layer of HAP nanocrystals in epitaxial orientation.

The thickness of the epitactically grown layer of nanocrystalline HAP is related to the ratio of the sintered CAP core material to HAP, said ratio being generally between 5:95 and 95:5, preferably from 10:90 to 90:10.

According to a frequently used embodiment the sintered CAP core material essentially consists of TCP, α-TCP being preferred.

The present invention further relates to a process of preparing the above porous biphasic calcium phosphate/hydroxyapatite (CAP/HAP) bone substitute material comprising the steps of (a) mixing a slurry of collagen fibers and a porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm, and (b) eliminating the water by vacuum suction.

The porous biphasic calcium phosphate/hydroxyapatite (CAP/HAP) bone substitute material may be a shaped body of porous CAP/HAP bone substitute material or a particulate or granulate of porous CAP/HAP.

According to a preferred embodiment the porous (CAP/HAP) bone substitute material is a particulate or a granulate of porous CAP/HAP bone substitute material, the impregnated collagen fibers then also acting as a binder between the particles or granules, thus providing a porous collagen matrix surrounding and impregnating particles or granules of porous CAP/HAP bone substitute material. Pieces cut from that matrix show some elastic properties which are of advantage for their use as implants.

The mixing of step (a) is generally a vigorous mixing, the latter being conveniently performed in the case of the above preferred embodiment in a mixer having a rotating blade.

Preferably the above process comprises the additional step of drying in a vacuum oven.

The present invention also relates to an implant which comprises a porous collagen matrix surrounding and impregnating particles or granules of porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm.

The present invention also concerns the use of the above defined CAP/HAP bone substitute material, generally in the form of a particulate or a shaped body as an implant or prosthesis for supporting bone formation, bone regeneration, bone repair and/or bone replacement at a defect site in a human or animal.

The present invention also relates to a method of promoting bone formation, bone regeneration and/or bone repair at a defect site in a human or animal by implanting the above defined CAP/HAP bone substitute material, generally in the form of a particulate or a shaped body.

The following examples illustrate the present invention without limiting its scope.

EXAMPLE 1

Preparation of a Bulk Sintered Material of α-TCP

For a mixture of 500 g (dry weight), 360 g dicalcium phosphate anhydrous powder, 144 g calcium carbonate powder and 220 ml deionized water were mixed for 7 minutes at 500 rpm using a laboratory stirrer. The slurry from the mixing process was immediately transferred into a high temperature stable platinum cup. The filled platinum cup was placed in a cold furnace. The furnace was heated to 1400° C. by using a heating rate of 60° C. per hour. The heating process was stopped after 72 hours by switching off the furnace. The sample was cooled down to room temperature within the furnace. The bulk sintered material (phase pure α-$Ca_3(PO_4)_2$) was removed from the furnace and the platinum cup. The bulk product from the sintering process had a weight of 420 g (weight loss 16.7%). The control of phase purity was performed using powder X-ray diffraction analysis.

EXAMPLE 2

Preparation of Porous Granules of Sintered α-TCP with a Particle Size Between 0.25 and 2 mm The bulk product from example 1 was crushed by using a jaw crusher (slot size 4 mm). The course granules were sieved by using a sieving machine and sieve inserts with mesh aperture 2 mm and 0.25 mm. After sieving the granule fractions were rinsed 2 times by using purified water for separating fine powder residuals adsorbed to the granules. The porous granules were dried for 10 hours at 120° C. in a cabinet dryer. The control of particle size distribution was done by using laser diffraction technology. The cleanness of the particle surfaces after rinsing was controlled by surface observation using scanning electron microscopy.

EXAMPLE 3

Preparation of Porous Cylinders (length 10 mm, diameter 6 mm) of Sintered α-TCP by CNC Milling The bulk product from example 1 was grinded to a cuboidal work piece with edge lengths a=3 cm, b=2 cm, c=2 cm using a grinding machine. The work piece was placed and fixed into a 4-axis CNC milling machine equipped with a round-head hard metal milling cutter tool with a diameter of 3 mm. The cylinders were milled by using a helical milling route with a radius of 3 mm and a slope of 0.25 mm. The main speed of the work piece during the CNC milling process was 1700 rotations per minute, the maximum rotation speed of the helical milling route was calculated by an integral process within the CNC equipment and averages 10 rotations per minute. After milling the cylindrical preforms were rinsed 2 times by using purified water for separating fine powder residuals adsorbed to the cylinder surface. The porous cylinders were dried for 10 hours at 120° C. in a cabinet dryer. The cleanness of the preform surface after rinsing was controlled by surface observation using scanning electron microscopy. The correctness of the preform dimensions was controlled by using a slide gauge.

EXAMPLE 4

Preparation of an Epitactically Grown Nanocrystalline HAP Coating on the Granules of Sintered α-TCP from Example 2

A buffered solution (1000 ml) adequate for the coating and phase transformation process was prepared by using 1.82 mol/l sodium, 4.68 mol/l hydrogen, 0.96 mol/1 phosphorus, 5.64 mol/l oxygen, 0.01 mol/l calcium and 0.71 mol/l chlorine. The solution will be adjusted to a pH of 7.4 at a temperature of 40° C. The granules produced according to example 1 and 2 were immersed into the prepared solution and stored within a well tempered water bath (40° C.) for a time calculated according a layer thickness at an average of 250 nm (10 hours) which equates to a phase composition of (w/w) 75% alpha-TCP and 25% hydroxyapatite. After immersing the granules were rinsed 3 times by purified water to remove residuals from the buffered solution. The porous granules were dried for 4 hours at 120° C. in a cabinet dryer. The phase composition of the granules were analyzed by Rietveld analysis of powder X-ray diffraction data, the crystal sizes of crystalline phases obtained by the coating process were analyzed by size-strain refinement of X-ray diffraction data according to the Bragg technique. The porosity of the granules was controlled by using mercury intrusion porosimetry, the surface morphology after coating was controlled by using scanning electron microscopy.

EXAMPLE 5

Preparation of an Epitactically Grown Nanocrystalline HAP Coating on the Cylinders of Sintered α-TCP from Example 3

A buffered solution (1000 ml) adequate for the coating and phase transformation process was prepared by using 1.82 mol/l sodium, 4.68 mol/l hydrogen, 0.96 mol/l phosphorus, 5.64 mol/l oxygen, 0.01 mol/l calcium and 0.71 mol/l chlorine. The solution was adjusted to a pH of 7.4 at a temperature of 40° C. The porous cylinders produced according to example 1 and 3 were immersed into the prepared solution and stored within a well tempered water bath (40° C.) for a time calculated according a layer thickness at an average of 20 μm (60 hours) which equates to a phase composition of approximately 85% (w/w) alpha-TCP and 15% (w/w) hydroxyapatite. After immersing the cylinders were rinsed 3 times by purified water to remove residuals from the buffered solution. The porous cylinders were dried for 10 hours at 120° C. in a cabinet dryer. The phase composition of the cylinders were analyzed by Rietveld analysis of powder X-ray diffraction data, the crystal sizes of crystalline phases obtained by the coating process were analyzed by size-strain refinement of X-ray diffraction data according to the Bragg technique. The epitaxial growth were analysed by using reflectance-difference (RD) spectroscopy. The porosity of the cylinders was controlled using mercury intrusion porosimetry, the surface morphology after coating was controlled using scanning electron microscopy. The layer thickness was controlled using reflection high-energy electron diffraction (RHEED) and/or photoelectron spectroscopy (XPS).

EXAMPLE 6

Influence of the Immersing Time on the Layer Thickness and the Phase Composition Tables 2 and 3 show experimental data for an example showing the influence of the immersing time on the layer thickness and the phase composition, respectively, for porous α-TCP particles with nearly spherical geometry and size from 10 to 20 μm, a porosity 25-40 vol. %, a specific (inner) surface area of 50-60 m$^2$/g, a bulk density of 0.6-0.8 g/ml.

TABLE 2

| Influence of the immersing time on the layer thickness | |
|---|---|
| Immersing time [min] | Layer thickness* [nm] |
| 0 | — |
| 15 | 37 (±10) |
| 30 | 112 (±4) |
| 60 | 121 (±9) |
| 600 | 238 (±8) |

*Epitaxy, chemical composition of the layer and layer thickness analysis were determined using RHEED (reflection high-energy electron diffraction) and XPS (photoelectron spectroscopy)

TABLE 3

| Influence of the immersing time on the phase composition | | |
|---|---|---|
| Immersing time [h] | TCP** [weight %] | HAP** [weight %] |
| 0 | 100 | — |
| 0.5 | 86.6 (±1) | 13.4 (±2) |
| 1 | 85.8 (±1) | 14.2 (±3) |
| 2 | 83.5 (±1) | 16.4 (±3) |
| 5 | 78.1 (±1) | 21.9 (±3) |
| 7.5 | 75.3 (±1) | 24.7 (±3) |
| 10 | 74.2 (±5) | 25.8 (±2) |
| 12 | 58.8 (±6) | 41.2 (±7) |
| 24 | 44.8 (±9) | 55.2 (±6) |
| 48 | 35.8 (±6) | 64.2 (±3) |
| 72 | — | 100 |

**Quantitative phase analysis was performed using Rietveld refinement of powder X-Ray diffraction data.
***Experimental data were evaluated on a system with following parameters: Liquid Phase: PBS buffered saline liquid, 20x, temperature 40° C.

EXAMPLE 7

Preparation of a Slurry of Collagen Fibres Derived From Pig Skin

Porcine hides were ground in a meat grinder to pieces of 1 to 20 mm. The water was removed using a water soluble solvent such as an alcohol or a ketone. The collagen fibres were defatted using a chlorinated hydrocarbon such as dichloroethane or methylene chloride or a non-chlorinated hydrocarbon such as hexane or toluene. After removing the solvent the collagen was treated with a strong inorganic base at a pH above 12 for a period of 6 to 24 hours and treated with a strong inorganic acid at a pH of 0 to 1 for a period of 1 to 12 hours. The excess acid was removed by rinsing with water and the suspension was homogenized to a 0.5 to 2% homogenous suspension of collagen fibres in the presence of a swelling regulator such as an inorganic salt. The suspension was dried by freeze-drying and the dry collagen fibres were successively cleaned with different organic solvents such as alcohols, ethers, ketones and chlorinated hydrocarbons, the solvents being then evaporated under vacuum to a solvent residue of less than 1%. A slurry of collagen fibres was prepared by mixing the cleaned dry fibres obtained above with water.

EXAMPLE 8

Preparation of a Plate of Porous (CAP/HAP) Bone Substitute Material Impregnated with Collagen Fibers 594.2 g of the slurry of collagen fibers (corresponding to about 14.855 g of dry collagen) prepared in Example 7 and 119.7 g of porous granules of (CAP/HAP) bone substitute material prepared as described in Example 5 and having a particle size between 0.5 and 1.0 mm were thoroughly mixed during 30 minutes and the mixture was poured into a suction filter and dried by suction. The plate of (CAP/HAP) bone substitute material impregnated with collagen fibers was carefully removed from the suction filter and dried in a vacuum oven at about 35° C. for 48 hours. Pieces of that plate were cut for in vivo testing.

The invention claimed is:

1. Porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral having a length of 30 to 46 nm and a width of 14 to 22 nm, which is impregnated with collagen fibers at a weight ratio of said collagen fibers to said porous biphasic calcium phosphate/hydroxyapatite (CAP/HAP) bone substitute material of at least 2%.

2. A porous CAP/HAP bone substitute material according to claim 1 wherein the weight ratio of said collagen fibers to said porous biphasic calcium phosphate/hydroxyapatite (CAP/HAP) bone substitute material is at least 5%.

3. A porous CAP/HAP bone substitute material according to claim 2 wherein the weight ratio of said collagen fibers to said porous biphasic calcium phosphate/hydroxyapatite (CAP/HAP) bone substitute material is at least 8%.

4. A porous CAP/HAP bone substitute material according to claim 1 wherein the weight ratio of said collagen fibers to said porous biphasic calcium phosphate/hydroxyapatite (CAP/HAP) bone substitute material is from 8 to 25%.

5. A porous CAP/HAP bone substitute material according to claim 1, wherein the collagen fibers are fibers of collagen type I, collagen type III or a mixture thereof.

6. A porous CAP/HAP bone substitute material according to claim 1, wherein the epitactically grown layer of nanocrystalline HAP generally has a thickness of at least from 15 to 50 nm.

7. A porous CAP/HAP bone substitute material according to claim 1 wherein the ratio of sintered CAP core material to HAP is between 5:95 and 95:5.

8. A porous CAP/HAP bone substitute material according to claim 1 wherein the ratio of sintered CAP core material to HAP is between 10:90 and 90:10.

9. A porous CAP/HAP bone substitute material according to claim 1 wherein the sintered CAP core essentially consists of $\alpha$-TCP.

10. A porous CAP/HAP bone substitute material according to claim 1 which comprises a particulate or a granulate of porous CAP/HAP bone substitute material impregnated with collagen fibers.

11. A porous CAP/HAP bone substitute material according to claim 1 which comprises a shaped body of porous CAP/HAP bone substitute material impregnated with collagen fibers.

12. A process of preparing a porous CAP/HAP bone substitute material according to claim 1, which comprises
(a) mixing a slurry of collagen fibers and a porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral having a length of 30 to 46 nm and a width of 14 to 22 nm, and
(b) eliminating the water by vacuum suction.

13. A process of claim 12 which further comprises the additional step of drying in a vacuum oven.

14. An implant or prosthesis for bone formation, bone regeneration, bone repair and/or bone replacement at a defect site in a human or animal comprising the porous biphasic CAP/HAP bone substitute material of claim 1.

15. A method of promoting bone formation, bone regeneration and/or bone repair at a defect site in a human or animal by implanting a CAP/HAP bone substitute material according to claim 1.

16. An implant which comprises a porous collagen matrix surrounding and impregnating particles or granules of porous biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral having a length of 30 to 46 nm and a width of 14 to 22 nm.

* * * * *